United States Patent

Reekers

Patent Number: 6,001,078
Date of Patent: Dec. 14, 1999

[54] SELECTIVE POSITIONING DRAINAGE CATHETER

[75] Inventor: Jan Albertus Reekers, Amstelveen, Netherlands

[73] Assignee: Cordis Corporation, Miami Lakes, Fla.

[21] Appl. No.: 08/864,116

[22] Filed: May 28, 1997

[30] Foreign Application Priority Data

May 29, 1996 [NL] Netherlands ............................ 1003226

[51] Int. Cl.⁶ ............................ A61M 25/00; A61B 17/22
[52] U.S. Cl. ............................... 604/43; 604/28; 604/35; 604/264
[58] Field of Search .............................. 604/35, 43, 52, 604/53, 239, 102, 169, 173, 258, 264, 267, 268, 272, 28; 600/486; D24/112; 606/159

[56] References Cited

U.S. PATENT DOCUMENTS

| | | | |
|---|---|---|---|
| 4,671,795 | 6/1987 | Mulchin | 604/281 |
| 4,747,840 | 5/1988 | Ladika et al. | 604/280 |
| 4,961,731 | 10/1990 | Bodicky et al. | 604/264 |
| 5,037,403 | 8/1991 | Garcia | 604/280 |
| 5,215,530 | 6/1993 | Hogan | 604/53 |
| 5,395,315 | 8/1995 | Griep | 604/35 |
| 5,681,274 | 10/1997 | Perkins et al. | 604/8 |
| 5,713,849 | 2/1998 | Bosma et al. | 604/28 |
| 5,713,851 | 2/1998 | Boudewijn et al. | 604/35 |

FOREIGN PATENT DOCUMENTS

| | | |
|---|---|---|
| 0 351 206 | 1/1990 | European Pat. Off. . |
| 0 693 295 | 1/1996 | European Pat. Off. . |
| WO 0005317 | 7/1988 | WIPO ..................... 604/53 |

Primary Examiner—Wynn Wood Coggins
Assistant Examiner—Sharon Finkel
Attorney, Agent, or Firm—Michael W. Montgomery

[57] ABSTRACT

A drainage catheter for selective positioning within the human vasculature which includes a catheter body defining separate pressure and discharge lumens. A connector means at a proximal end of the catheter connects the pressure channel to a source of liquid under pressure. An inlet opening is positioned in the side of the catheter adjacent the distal end thereof and communicates with the discharge channel. The pressure channel extends from the proximal end distally forward of the inlet opening and then curves rearwardly to join the discharge channel at said inlet opening. The pressure channel is shaped to form a spray nozzle to direct pressurized fluid in the pressure channel across said inlet opening and into the discharge channel to create a suction adjacent the inlet opening. A preformed distal tip portion extends from the distal end of the drainage catheter. The preformed tip portion is formed of a material having the characteristic of retaining a plastic memory and is preformed into a curved configuration for selective positioning.

4 Claims, 3 Drawing Sheets

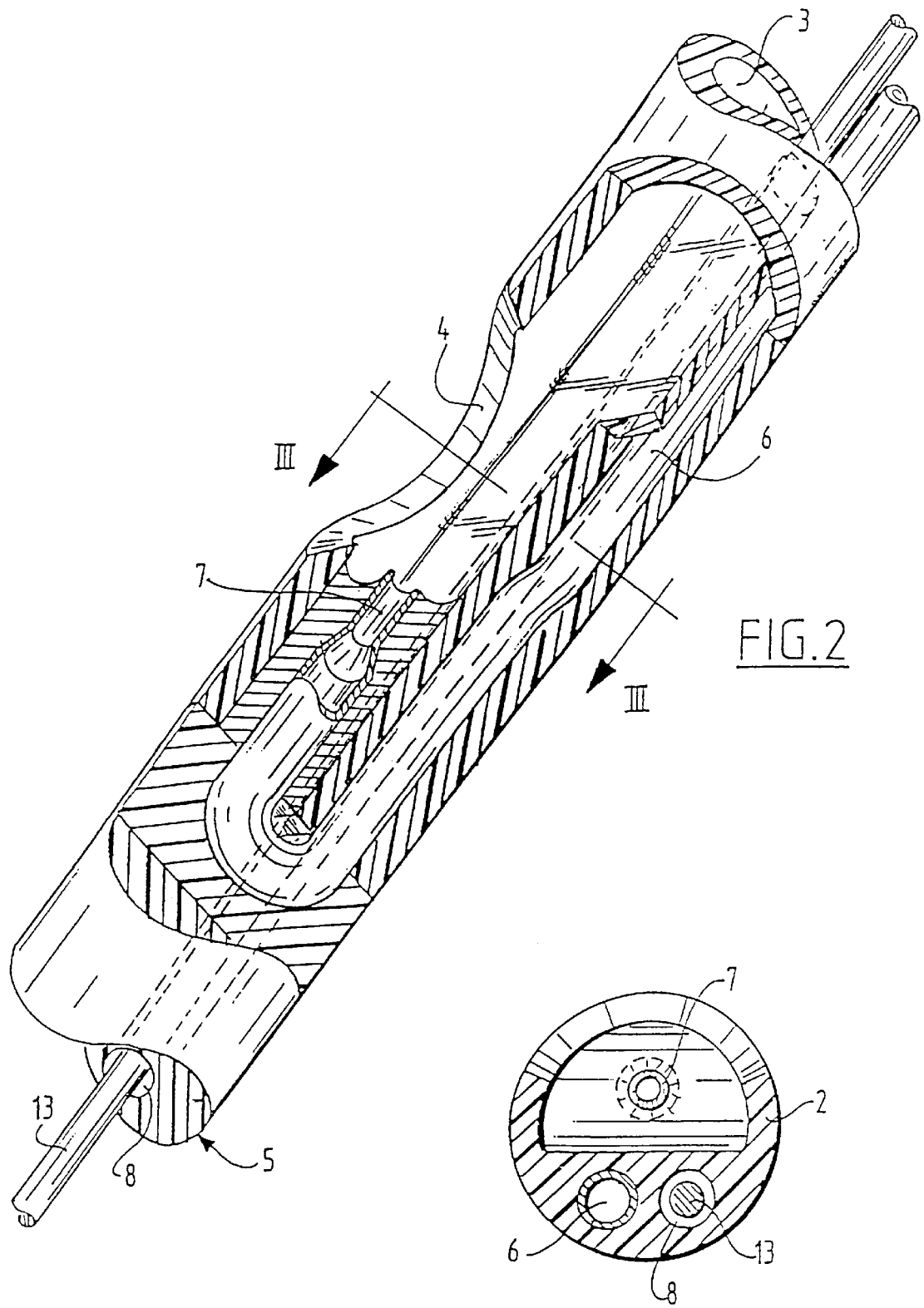

SELECTIVE POSITIONING DRAINAGE CATHETER

BACKGROUND OF THE INVENTION

1. Field of the Invention

The present invention relates to a drainage catheter which may be inserted into a human vessel for removing blood clots, plaque and other such debris.

2. Description of the Prior Art

Prior art drainage catheters have included a pressure channel which extends along the length of the catheter and which forms a tongue at the distal end of the catheter, which in turn curves back to a discharge channel. A spray nozzle is formed at the tip of the tongue to deliver a liquid jet of fluid. For removing liquids or solid particles, the discharge channel may be connected to a suction pump, or alternatively may just empty into a collection reservoir. The jet of fluid which is delivered by the spray nozzle is used for breaking up, or crushing, solid particles and for removing the solid particles, or deposits, from the vessels of the body.

The present invention has for its object a drainage catheter system of the type described above which can be introduced into blood vessels and which may be selectively positioned to a desired location without damaging the vascular system. Specifically, the catheter of this invention may be used without the usual difficulty which is encountered in positioning the distal tip of the catheter associated with prior drainage catheter systems.

SUMMARY OF THE INVENTION

With this invention, a drainage catheter is provided which comprises a cylindrical catheter body having a pair of separate lumens defined within the body to form a pressure channel and a discharge channel. Connector means are provided at the proximal end of the catheter for connecting the pressure channel and the discharge channel to a source of pressurized liquid and to a discharge container.

At the distal end of the catheter, the discharge channel defines an inlet opening which is formed in a side wall of the catheter body. The pressure channel is also defined within the body to extend forwardly toward the distal end beyond the inlet opening, and then to bend back approximately 180 degrees and to extend again a short distance rearwardly. A spray nozzle is provided at the distal end of the pressure channel to direct a liquid jet of fluid from the pressure channel to the discharge channel. The discharge channel is adjacent to the inlet opening to cause a suction to be created through the inlet opening by aspiration, or by ejector action. Thus, a suction occurs at the location of the side inlet opening. Preferably, the spray nozzle is constricted by a tapered nozzle and is positioned distally of the side inlet opening.

The source of liquid under pressure is all that is required for the operation of the catheter, however, a suction pump may be used to increase the suction if desired. With very long, small diameter catheters a suction pump may be used to augment the suction due to the aspiration action. During use, the feed of the liquid under pressure may be controlled as to pressure, or flow rate, with the suction generated being directly dependent on this feed of liquid. With the catheter according to the invention, liquids, soft deposits, and solid particles may be removed from the body.

Preferably, the catheter carries adjacent its distal end a rigid "J" or "U"-shaped tube which is sealingly positioned with at least one leg of the U-shaped tube in the pressure channel, and with a second leg thereof communicating with the discharge channel. The end of the second leg of the U-shaped tube is positioned adjacent to and preferably generally upstream of the inlet opening. Thus, the U-shaped channel defines the reverse bending portion of the flow path described above and also the nozzle where the discharge channel and the pressure channel meet adjacent the distal end. Thus, the cross-sectional shape of the pressure channel in the reversely bending portion and the nozzle may in this way be very precisely controlled and dimensioned, such that the flow of the liquid under pressure out of the pressure channel and past the inlet opening can create the precisely desired aspiration or ejector action with great reliability. Typically the U-shaped tube is made of a metal such as stainless steel.

Preferably, the second leg of the U-shaped tube is narrowed toward its free end, positioned adjacent the inlet opening so as to form a jet nozzle for creation of effective suction pressure by the aspiration effect as rapidly moving pressurized fluid passes across the inlet opening and down the discharge channel. Even with catheters having a very small diameter, a reliable suction action by aspiration may be obtained in this manner.

As mentioned before, the catheter according to the invention may be used with X-ray contrast fluid as the liquid under pressure. It is preferable for the pressure channel to be connected at its proximal end to a pressurized source of liquid, while the discharge channel is connected at its proximal end to a syringe, or another receptacle, for waste fluid received from the discharge channel. A syringe, or similar expansible chamber, connected to the discharge channel may be used to block the discharge flow through the discharge channel by holding stationary the syringe plunger, thus preventing fluid flow into the syringe. When in that condition, the X-ray contrast fluid will necessarily flow out of the inlet opening, in that way making visible the surroundings area in front end for the catheter. In this condition, the catheter may be maneuvered into a desired position, for example near a blood clot deposit in a vessel. Subsequently the plunger of the syringe may be pulled back, so that space in the syringe is created for taking up fluid that is sucked into the discharge channel. By suitable manipulating the plunger of the syringe, the suction through the inlet opening may also be increased or decreased, with the suction being primarily from aspiration effects.

In accordance with the present invention, there is provided a drainage catheter for selective positioning within the human vasculature which includes a flexible, tubular basic catheter body defining two separate catheter lumens. The lumens comprise a pressure channel and a discharge channel. A connector at a proximal end of the catheter couples the pressure channel to a source of liquid under pressure and the discharge channel to discharge means respectively. An inlet opening is positioned in the side of the catheter adjacent the distal end of the catheter. The discharge channel communicates with the inlet opening and the pressure channel extends from the proximal end distally forward of the inlet opening and then curves rearwardly to join the discharge channel at the inlet opening. The pressure channel defines a spray nozzle to direct pressurized fluid in the pressure channel across the inlet opening and into the discharge channel to create a suction adjacent to the inlet opening. The improvement comprises a preformed distal tip portion extending from the distal end of the drainage catheter. The preformed tip portion is formed of a material having the characteristic of retaining a plastic memory and is preformed into a curved configuration for such selective positioning.

In accordance with another aspect of the present invention, the drainage catheter also includes a guidewire lumen which extends through the tubular basic catheter body from the proximal end to the distal end thereof A guidewire lumen extends through at least a portion of the distal tip portion and is in communication with the guidewire lumen within the catheter body. A straight guidewire is slidably positioned within the guidewire lumen of the catheter body such that when the guidewire is moved to a position so that it extends into the distal tip portion, the curved preformed distal tip portion becomes straightened.

In accordance with still another aspect of the present invention, the distal tip portion is formed into a spiral curve configuration.

In accordance with a further aspect of the present invention, the distal tip portion is curved such that the spiral shape extends away from the side of the catheter body on the same side of the catheter body as the inlet opening.

The invention may be better understood by the following description with reference to the figures of the preferred embodiment.

BRIEF DESCRIPTION OF THE DRAWINGS

FIG. 2 shows an enlarged detail indicated by arrow II in FIG. 1;

FIG. 3 illustrates a cross-section along the line III—III in FIG. 2; and,

DESCRIPTION OF A PREFERRED EMBODIMENT

Figure 1:
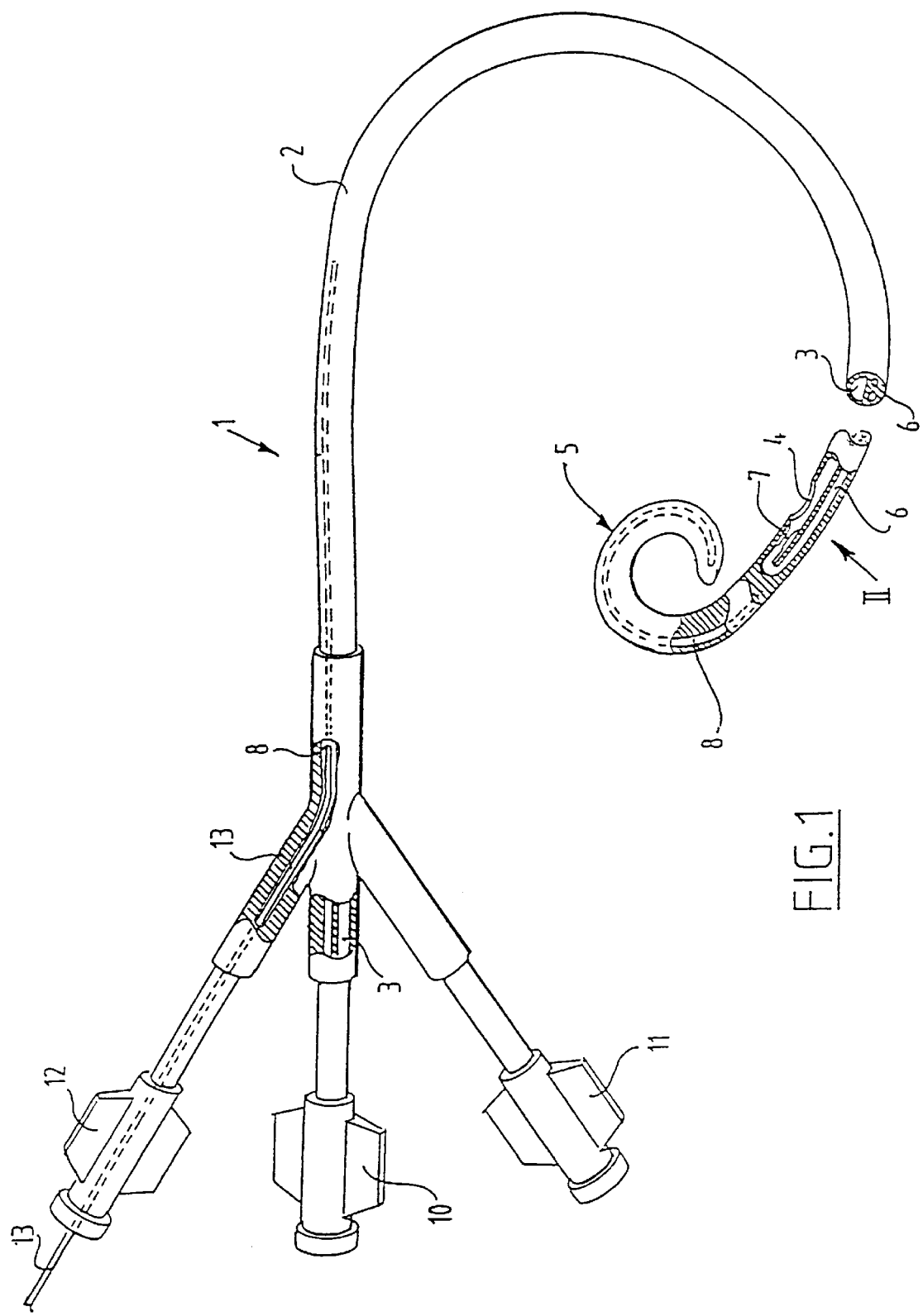
FIG. 1 illustrates a partly broken away view of a suction catheter according to an embodiment of the invention.

The catheter 1 illustrated in FIG. 1 comprises a basic body 2, which includes a suction inlet 4 which takes the form of passageway extending through the wall of the catheter body 2. The suction inlet 4 is connected with a discharge lumen, which extends from the inlet 4 to the proximal end of the catheter. There the discharge lumen 3 is completed to a discharge connector 10. From the suction inlet 4, a preformed, curved and pliable tip 5 extends from the distal end of the catheter body 4. The tip is preformed into a "pigtail" configuration.

As can be seen in the FIG. 1, the tip 5 is curved away from the axis of the catheter body in the direction in which the suction inlet 4 is pointing. As a result, the suction inlet 4 is at all times kept at a certain distance from the wall of a blood vessel into which the catheter has been introduced.

The catheter shown in FIG. 1 is a preferred embodiment wherein the suction action at the suction inlet 4 is effected by means of ejector action. A pressure lumen 6 has been arranged inside the basic body 2 which ends close to the relatively distal end of the suction inlet 4, that is to say on the left-hand side in FIG. 1, in a jet nozzle 7 which is directed in the opposite, proximal direction along the suction inlet in the discharge lumen 3.

As can be seen in greater detail in FIG. 2, a fluid jet can be directed along the opening 4 by means of the jet nozzle 7, as a result of which suction will be generated at the suction inlet 4 due to the ejector action. The material sucked in will be passed along by the liquid released from the jet nozzle 7 through the discharge lumen 3 to the discharge connector 10.

At the proximal end the pressure lumen 6 is connected to a pressure connector 11.

For the purpose of introducing the catheter 1, the curved tip 5 can be straightened by using a guidewire 13, which is advanced through a guidewire lumen 8 arranged for that purpose inside the basic body 2. At the proximal end this guidewire lumen 8 is connected with a guidewire connection 12.

Figure 4:
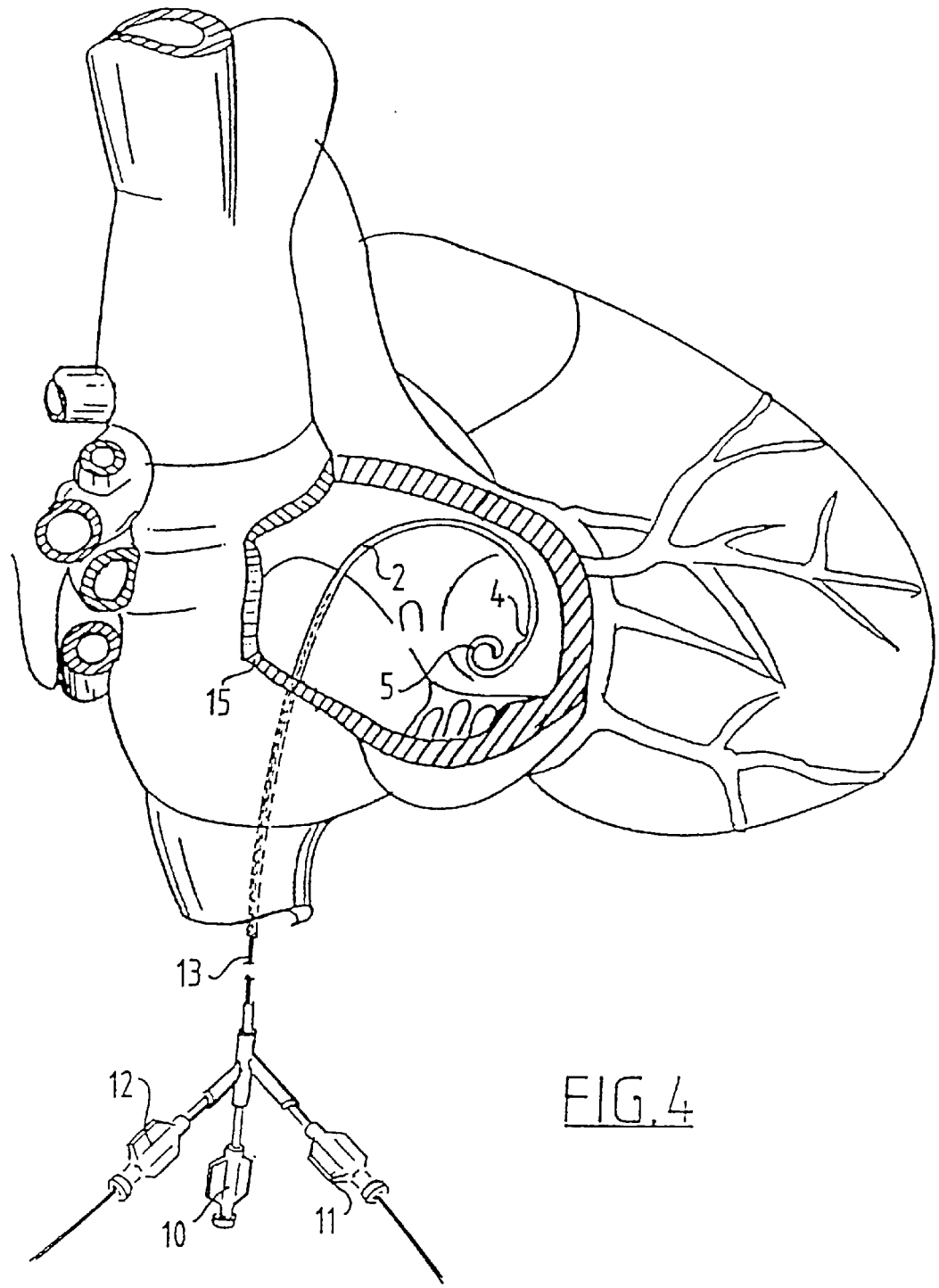
FIG. 4 illustrates schematically the use of the suction catheter.

It should be noted that the connectors 10, 11 and 12 in the FIGS. 1 and 4 have only been illustrated schematically. A catheter used for the purpose described will have been provided at the proximal end with hemostatic devices in order to prevent undesired leaking out of blood via the lumens of the catheter.

As can be seen in FIG. 4, the catheter 1 with the curved preformed tip 5 can be employed in large blood vessels and even by advanced through the heart 15 into the pulmonary artery. Because of the preformed curve, the suction inlet 4 is positioned in a stable manner as required. The suction inlet 4 cannot attach itself to the wall as it is kept, by means of the curve 5, at a certain distance from the walls of the blood vessel.

Although the guidewire lumen in the example of an embodiment shown extends right from the proximal end to the distal end, the catheter according to the invention can also be given the embodiment of a rapid exchange type. In that case the guidewire lumen extends from an opening in the wall of the basic body 2 positioned at a limited distance from the distal end to the distal end. With such an embodiment the guidewire lumen can be formed in the end section only in a suitable manner. In that case the guidewire lumen does not take up any space in the section of the basic body through which the discharge lumen 3 and the pressure lumen 6 extend. These can in that case be given an optimum cross section for the purpose of ejector action.

The tip may be connected to the remaining part of the catheter in any suitable manner. For instance by means of glueing or welding. The specific shape of the curve may be adapted to the required operative position. The tip may have been manufactured in a suitable manner of a plastic material opaque to X-rays, so that the tip can be made properly visible on an X-ray screen.

Although the preferred embodiment shown and described has a unique configuration, the advantages of the invention do not stem from only that embodiment or technique but from the invention as claimed.

What is claimed is:

1. A drainage catheter for selective positioning within the human vasculature, wherein said drainage catheter comprises a flexible, tubular basic catheter body defining a first and second catheter lumen respectively comprising a pressure channel and a discharge channel;

a connector at a proximal end of said catheter for respectively connecting the pressure channel to a source of liquid under pressure, and the discharge channel to discharge means;

an inlet opening positioned in a side wall of said catheter adjacent the distal end thereof, said discharge channel communicating with said inlet opening, said pressure channel extending from said proximal end to a point distal of said inlet opening and then curving rearwardly to join said discharge channel at said inlet opening, said pressure channel defining a spray nozzle to direct pressurized fluid in the pressure channel across said inlet opening and into said discharge channel to create a suction adjacent said inlet opening, wherein the side wall of said catheter is substantially imperforate except for the inlet opening and a preformed distal tip portion extending from the distal end of the drainage catheter, said preformed tip portion being formed of a material having the characteristic of retaining a plastic memory and being preformed into a curved spiral configuration for such selective positioning;

wherein said pressure channel provides fluid communication only between said inlet opening and said source of liquid under pressure, and said discharge channel provides fluid communication only between said inlet opening and said discharge means.

2. A drainage catheter as defined in claim 1, further comprising a proximal guidewire lumen which extends through the tubular basic catheter body from the proximal end to the distal end thereof, a distal guidewire lumen which extends through at least a portion of the distal tip portion and being in communication with the proximal guidewire lumen within the catheter body, wherein the proximal and distal guidewire lumens are adapted to slidably receive a guidewire, such that when the guidewire is moved to a position so that it extends into the distal tip portion, the curved preformed distal tip portion tends to straighten.

3. A drainage catheter as defined in claim 1, wherein the spiral configuration of the tip portion extends in a single plane which plane is parallel to the central axis of the catheter body.

4. A drainage catheter as defined in claim 3, wherein the distal tip portion is curved such that the spiral shape extends in a direction away from the side of the catheter body and on the same side of the catheter body as the inlet opening.

* * * * *